United States Patent
Sun

(10) Patent No.: US 12,024,730 B1
(45) Date of Patent: Jul. 2, 2024

(54) GRANULE FOR DETECTING GLUCOSE IN PET URINE AND METHOD FOR PREPARING THE SAME

(71) Applicant: Shandong Ruida Silica Gel Co., Ltd., Linyi (CN)

(72) Inventor: Qinbin Sun, Linyi (CN)

(73) Assignee: SHANDONG RUIDA SILICA GEL CO., LTD., Linyi (CN)

( * ) Notice: Subject to any disclaimer, the term of this patent is extended or adjusted under 35 U.S.C. 154(b) by 0 days.

(21) Appl. No.: 18/516,940

(22) Filed: Nov. 21, 2023

(30) Foreign Application Priority Data

Jul. 17, 2023 (CN) .......................... 202310869785.5

(51) Int. Cl.
| | | |
|---|---|---|
| *C12N 9/98* | (2006.01) | |
| *C12N 9/04* | (2006.01) | |
| *C12N 9/08* | (2006.01) | |
| *C12Q 1/54* | (2006.01) | |

(52) U.S. Cl.
CPC ............. *C12N 9/98* (2013.01); *C12N 9/0006* (2013.01); *C12N 9/0065* (2013.01); *C12Q 1/54* (2013.01); *C12Y 101/03004* (2013.01); *C12Q 2326/50* (2013.01); *C12Q 2326/96* (2013.01); *G01N 2333/904* (2013.01); *G01N 2333/908* (2013.01)

(58) Field of Classification Search
CPC ...... C12N 9/98; C12N 9/0006; C12N 9/0065; C12Q 1/54; C12Y 101/03004
See application file for complete search history.

(56) References Cited

U.S. PATENT DOCUMENTS

| 10,175,231 B2 * | 1/2019 | Jollez ...................... C12Q 1/54 |
| 2007/0185001 A1 * | 8/2007 | Baur .................. C11D 17/0039 |
| | | 510/392 |
| 2015/0238931 A1 * | 8/2015 | Lipscomb ............ B01J 20/3212 |
| | | 502/404 |

* cited by examiner

*Primary Examiner* — Ruth A Davis
(74) *Attorney, Agent, or Firm* — MATTHIAS SCHOLL P.C.; Matthias Scholl

(57) ABSTRACT

A granule for detecting glucose in pet urine, includes: 80-100 parts by weight of a filler, 30-50 parts by weight of water-absorbent material, 2-4 parts by weight of a bacteriostatic agent, 5-10 parts by weight of an adhesive, 1-2 parts by weight of glucose oxidase, 2-4 parts by weight of peroxidase, 2-6 parts by weight of an indicator.

4 Claims, No Drawings

GRANULE FOR DETECTING GLUCOSE IN PET URINE AND METHOD FOR PREPARING THE SAME

CROSS-REFERENCE TO RELATED APPLICATIONS

Pursuant to 35 U.S.C. § 119 and the Paris Convention Treaty, this application claims foreign priority to Chinese Patent Application No. 202310869785.5 filed Jul. 17, 2023, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a granule for detecting glucose in pet urine and a method for preparing the same.

Pets are good friends that bring happiness and companionship to people. However, pets are prone to diseases, and due to language barriers, when they suffer from serious symptoms, it may be difficult to treat. Glucose level in the urine is an important indicator for health examination of pets. Some pet hospitals may provide checkup services for pets, but the hospitals are thinly distributed, and the fees are expensive.

SUMMARY

To solve the aforesaid problems, the disclosure provides a granule for detecting glucose in pet urine and a method for preparing the same.

The granule for detecting glucose in pet urine comprises 80-100 parts by weight of a filler, 30-50 parts by weight of water-absorbent material, 2-4 parts by weight of a bacteriostatic agent, 5-10 parts by weight of an adhesive, 1-2 parts by weight of glucose oxidase, 2-4 parts by weight of peroxidase, 2-6 parts by weight of an indicator.

In a class of this embodiment, the filler is wood fiber, gelatinized starch, bentonite clay, charcoal of crop residue, acrylic fiber, polyacrylonitrile fiber, or a mixture thereof.

In a class of this embodiment, the water-absorbent material is acrylic-epoxy high absorbent resin.

In a class of this embodiment, the bacteriostatic agent is benzyl dichloride, ethyl paraben, potassium sorbate, sodium benzoate, or a mixture thereof.

In a class of this embodiment, the adhesive is styrene-butadiene rubber, polyurethane, cellulose nitrate, sodium carboxymethyl cellulose, polyvinyl alcohol, or a mixture thereof.

In a class of this embodiment, the indicator is a mixture of 4-aminoantipyrine and sodium 4-hydroxybenzoate mixed in a 1:1 weight ratio.

Further provided is a method for preparing the granule for detecting glucose in pet urine comprising:
1) weighing the filler, the water-absorbent material, the bacteriostatic agent, the adhesive, glucose oxidase, peroxidase, and the indicator according to corresponding weight parts thereof as raw materials; 2) pulverizing solid components of the raw materials in 1);
3) mixing pulverized solid components obtained in 2) and liquid components of the raw materials in 1), and adding water to a resulting mixture to yield a mixed slurry, wherein the added water is 0.4-0.6 times of a total mass of the raw materials;
4) feeding the mixed slurry to a twin-screw extruder for granulation, to yield a granule; and
5) drying the granule.

In a class of this embodiment, after being pulverized, the solid components are screened using a 100-mesh sieve.

In a class of this embodiment, a working temperature of the twin-screw extruder is controlled at 50-60° C.; a length of the granule is 20 mm, and a diameter of 9 mm.

In a class of this embodiment, the granule is dried at 75-85° C. for 2-3 hours.

The following advantages are associated with the granule for detecting glucose in pet urine and a method for preparing the same:

The granule is placed in a pet's urine excretion area such as a cat litter basin, so that the granule comes into full contact with urine. If urine contains glucose, it will be oxidized by glucose oxidase to produce glucuronic acid and hydrogen peroxide. Hydrogen peroxide reacts with the indicator to change color under the action of peroxidase, and then the glucose content can be determined by whether the color changes and the intensity of the color.

DETAILED DESCRIPTION

To further illustrate the disclosure, embodiments detailing a granule for detecting glucose in pet urine and a method for preparing the same are described below. It should be noted that the following embodiments are intended to describe and not to limit the disclosure.

Example 1

1) Weighing 80 g of bentonite clay, 30 g of acrylic-epoxy high absorbent resin, 2 g of potassium sorbate, 5 g of styrene-butadiene rubber, 1 g of glucose oxidase, 2 g of peroxidase, 1 g of 4-aminoantipyrine, and 1 g of sodium 4-hydroxybenzoate as raw materials;

2) pulverizing solid components of the raw materials in 1), and screening the pulverized solid components using a 100-mesh sieve;

3) mixing the screened solid components obtained in 2) and liquid components of the raw materials in 1), and adding water to a resulting mixture to yield a mixed slurry, where the added water is 0.4 times of a total mass of the raw materials;

4) feeding the mixed slurry to a twin-screw extruder having a working temperature of 50° C. for granulation, to yield a granule having a length of 20 mm, and a diameter of 9 mm; and 5) drying the granule at 75° C. for 3 hours, to yield a granule for detecting glucose in pet urine.

Example 2

1) Weighing 20 g of wood fiber, 40 g of bentonite clay, 20 g of charcoal of crop residue, 20 g of acrylic fiber, 50 g of acrylic-epoxy high-absorbent resin, 3 g of ethyl paraben, 1 g of sodium benzoate, 3 g of styrene-butadiene rubber, 5 g of cellulose nitrate, 2 g of sodium carboxymethyl cellulose, 1-2 g of glucose oxidase, 2-4 g of peroxidase, 3 g of 4-aminoantipyrine and 3 g of sodium 4-hydroxybenzoate as raw materials;

2) pulverizing solid components of the raw materials in 1), and screening the pulverized solid components using a 100-mesh sieve;

3) mixing the screened solid components obtained in 2) and liquid components of the raw materials in 1), and adding water to a resulting mixture to yield a mixed slurry, where the added water is 0.6 times of a total mass of the raw materials;

4) feeding the mixed slurry to a twin-screw extruder having a working temperature of 60°C for granulation, to yield a granule having a length of 20 mm, and a diameter of 9 mm; and 5) drying the granule at 75° C. for 3 hours, to yield a granule for detecting glucose in pet urine.

Example 3

1) Weighing 10 g of wood fiber, 15 g of gelatinized starch, 15 g of bentonite clay, 20 g of charcoal of crop residue, 10 g of acrylic fiber, 10 g of polyacrylonitrile fiber, 40 g of acrylic-epoxy high absorbent resin, 0.5 g of benzyl dichloride, 1 g of ethyl paraben, 1 g of potassium sorbate, 0.5 g of sodium benzoate, 1.5 g of styrene-butadiene rubber, 2 g of polyurethane, 1 g of cellulose nitrate, 2 g of sodium carboxymethyl cellulose, 1 g of polyvinyl alcohol, 1 g of glucose oxidase, 3 g of peroxidase, 2 g of 4-aminoantipyrine, and 2 g of 4-hydroxybenzoate as raw materials;

2) pulverizing solid components of the raw materials in 1), and screening the pulverized solid components using a 100-mesh sieve;

3) mixing the screened solid components obtained in 2) and liquid components of the raw materials in 1), and adding water to a resulting mixture to yield a mixed slurry, where the added water is 0.5 times of a total mass of the raw materials;

4) feeding the mixed slurry to a twin-screw extruder having a working temperature of 55° ° C. for granulation, to yield a granule having a length of 20 mm, and a diameter of 9 mm; and 5) drying the granule at 75° C. for 2.5 hours, to yield a granule for detecting glucose in pet urine.

The granules for detecting glucose in pet urine prepared in Examples 1-3 were added to 2.2 mmol/L glucose solution, respectively, and the result was that the granules in Examples 1-3 all showed red. 2.2 mmol/L is the upper limit of the glucose content of normal pet urine, so the granules prepared by the disclosure are able to change to red through color reaction when the sugar content of the pet's urine exceeds the standard.

It will be obvious to those skilled in the art that changes and modifications may be made, and therefore, the aim in the appended claims is to cover all such changes and modifications.

What is claimed is:

1. A method for preparing granules for detecting glucose in pet urine, the method comprising:
   1) weighing raw materials; the raw materials comprising between 80 and 100 weight parts of a filler, between 30 and 50 weight parts of a water-absorbent material, between 2 and 4 weight parts of a bacteriostatic agent, between 5 and 10 weight parts of an adhesive, between 1 and 2 weight parts of glucose oxidase, between 2 and 4 weight parts of peroxidase, and between 2 and 6 weight parts of an indicator; wherein:
   the filler is wood fiber, gelatinized starch, bentonite clay, charcoal of crop residue, acrylic fiber, polyacrylonitrile fiber, or a mixture thereof;
   the water-absorbent material is an acrylic-epoxy resin;
   the bacteriostatic agent is ethyl paraben, potassium sorbate, sodium benzoate, or a mixture thereof;
   the adhesive is styrene-butadiene rubber, polyurethane, cellulose nitrate, sodium carboxymethyl cellulose, polyvinyl alcohol, or a mixture thereof; and
   the indicator is a mixture of 4-aminoantipyrine and sodium 4-hydroxybenzoate at a weight ratio of 1:1;
   2) pulverizing the filler, the water-absorbent material, the bacteriostatic agent, the glucose oxidase, the peroxidase, and the indicator;
   3) mixing the filler, the water-absorbent material, the bacteriostatic agent, the glucose oxidase, the peroxidase, and the indicator obtained in 2) with the adhesive, and adding water to a resulting mixture to yield a mixed slurry, wherein an amount of the water is 0.4-0.6 times of a weight of the raw materials;
   4) feeding the mixed slurry to a twin-screw extruder for granulation, to yield granules; and
   5) drying the granules.

2. The method of claim 1, wherein the method further comprises passing the filler, the water-absorbent material, the bacteriostatic agent, the glucose oxidase, the peroxidase, and the indicator through a 100-mesh sieve after being pulverized in 2).

3. The method of claim 1, wherein a working temperature of the twin-screw extruder is controlled at 50-60° C.; a length of the granules is 20 mm, and a diameter of the granules is 9 mm.

4. The method of claim 1, wherein the granules are dried in 5) at 75-85° C. for 2-3 hours.

* * * * *